(12) United States Patent
Richelsoph et al.

(10) Patent No.: US 8,585,705 B2
(45) Date of Patent: Nov. 19, 2013

(54) PERCUTANEOUS INSTRUMENTATION AND SURGICAL PROCEDURE

(71) Applicant: Intelligent Implant Systems, LLC, Charlotte, NC (US)

(72) Inventors: Marc Evan Richelsoph, Belmont, NC (US); David Frederick Waller, Charlotte, NC (US)

(73) Assignee: Intelligent Implant Systems, LLC, Charlotte, NC (US)

( * ) Notice: Subject to any disclaimer, the term of this patent is extended or adjusted under 35 U.S.C. 154(b) by 0 days.

(21) Appl. No.: 13/654,014

(22) Filed: Oct. 17, 2012

(65) Prior Publication Data

US 2013/0096637 A1 Apr. 18, 2013

Related U.S. Application Data

(60) Provisional application No. 61/548,571, filed on Oct. 18, 2011.

(51) Int. Cl.
*A61B 17/70* (2006.01)

(52) U.S. Cl.
USPC ............................ 606/86 A; 606/99; 606/104

(58) Field of Classification Search
USPC .................... 606/246, 261, 96, 99, 104, 86 A
See application file for complete search history.

(56) References Cited

U.S. PATENT DOCUMENTS

| | | |
|---|---|---|
| 2005/0070917 A1 | 3/2005 | Justis |
| 2009/0326586 A1 | 12/2009 | Duarte |
| 2010/0222817 A1 | 9/2010 | Perez-Cruet et al. |
| 2011/0106187 A1 | 5/2011 | Foley et al. |

*Primary Examiner* — Mary Hoffman
*Assistant Examiner* — Christina Negrellirodriguez
(74) *Attorney, Agent, or Firm* — Mayback & Hoffman, P.A.; Gregory L. Mayback

(57) ABSTRACT

An instrument for assisting in guiding a spinal connector or rod through one or more spinal implants placed in the spine includes a main assembly having the ability to accurately guide a rod through the implants by way of rotation and translation. By introducing the rod via rotation, the tip of the rod can be located very accurately deep in soft tissue for percutaneous applications. Once inside the first implant, the rod tip can be advanced by translation and rotation to the next implant. The number of implants connected in this manner is only limited to the length and curvature of the rod introduced. However, an advantage to the instrument is the ability to handle multiple length rods of different curvatures by adjustments to the instrument.

3 Claims, 13 Drawing Sheets

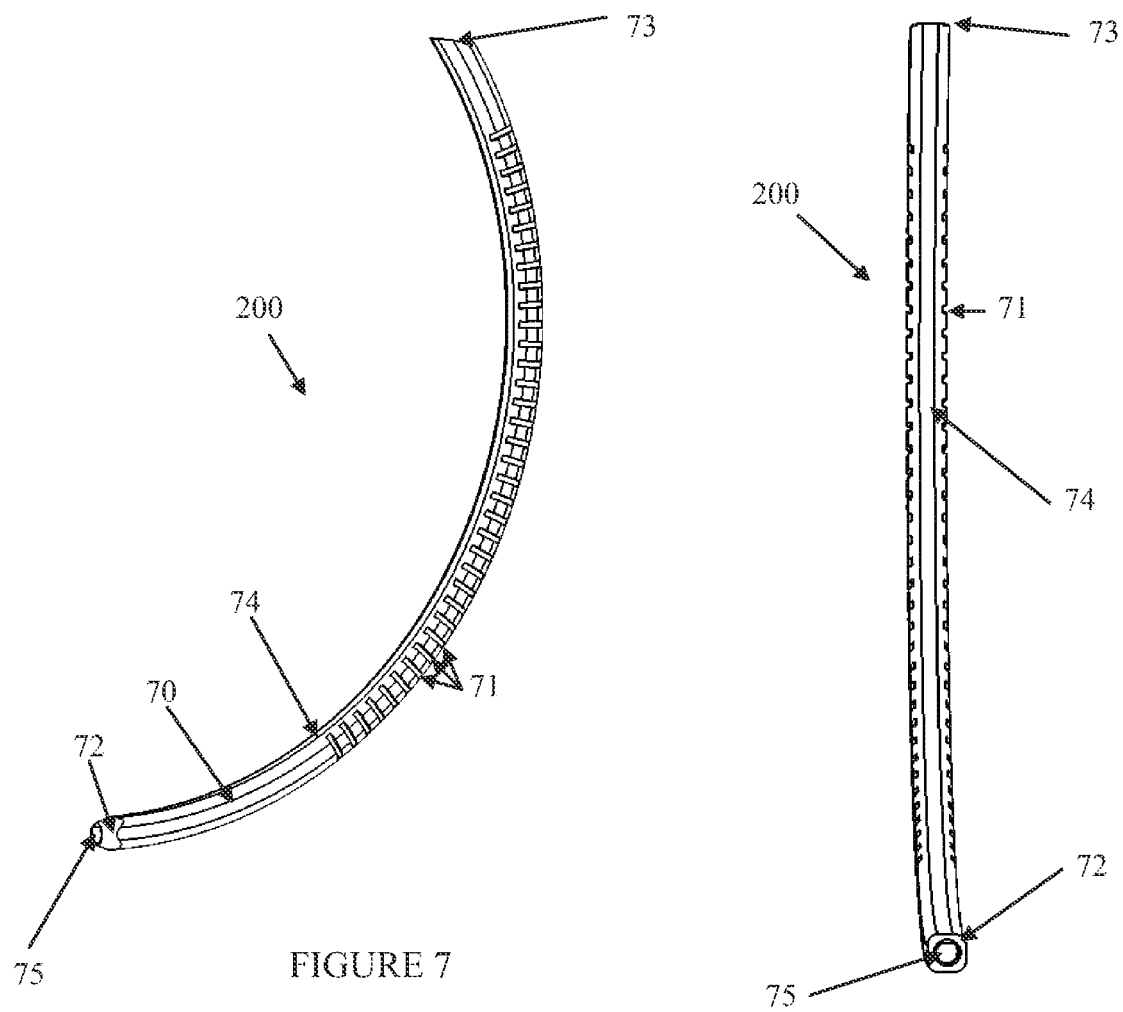
FIGURE 7
FIGURE 8
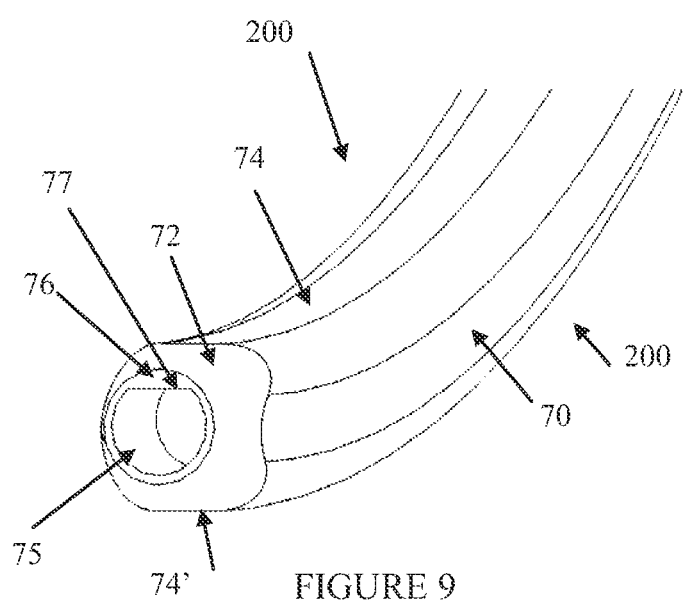
FIGURE 9

PERCUTANEOUS INSTRUMENTATION AND SURGICAL PROCEDURE

CROSS-REFERENCE TO RELATED APPLICATIONS

This application claims the priority, under 35 U.S.C. §119, of co-pending U.S. Provisional Patent Application Ser. No. 61/548,571, filed Oct. 18, 2011; the prior application is herewith incorporated by reference herein in its entirety.

STATEMENT REGARDING FEDERALLY SPONSORED RESEARCH OR DEVELOPMENT

Not Applicable

FIELD OF THE INVENTION

The present invention lies in the field of spinal implants. The present disclosure relates to instrumentation and surgical procedure for percutaneous insertion of spinal implants. More specifically, the present invention relates to an instrument that assists in guiding a connecting member between two or more implants under the skin with minimal damage to the underlying muscle and a surgical technique for using the instrument. This provides the benefits of more accurate and easier measures of connecting two or more implants while minimizing patient trauma and reducing surgical recovery time.

BACKGROUND OF THE INVENTION

The insertion of pedicle screws into the spine for fixation has been commonly used for many years. In general, a set of implants is placed on both sides of the spinous process into the pedicles and the set on each side is connected by an individual rod. For example, in a single level fusion, whereby two vertebral bodies are intended to be fused together, four pedicle screws are used, two on each side of the spinous process. Each set of two is then connected by the rod. For multiple levels, more screws are used and connected by longer rods. The general technique is an open procedure, whereby the incision in the skin is long and spans the length of the affected area of the spine to be treated. To reach the spine, the incision is continued through the muscle. These long incisions are painful and require significant healing time. In some cases, where spinal pathology is complicated, this may be the only prudent approach. However, in many cases, a less traumatic procedure would be highly beneficial in reducing patient pain and speeding recovery time.

The current concepts for minimally invasive surgical approaches for placing pedicle screws generally fall into two basic forms. Sextant, which is an instrument covered under U.S. Pat. No. 6,530,929 to Justis et al. and U.S. Pat. No. 7,008,422 to Foley et al., uses an instrument that swings the connecting rod through an arc. This configuration requires that all the implants be on the arc. To accomplish this alignment, the implants are connected to towers that are subsequently connected together to create a single pivot point. The connecting rod must be swept around this pivot point to pass through all the implants connected to the towers. This procedure is very problematic. First, the spine is not a uniform curve. Disadvantageously, the instrument requires the spine to be forced into a uniform curve. Secondly, the pedicles are at angles that vary from level to level. This complicates placing of the instrument. To make such an instrument function, the number of implants that can be surgically connected is very limited. The second basic form for placing pedicle screws is that of attaching extensions, or towers, to the implants to lengthen the implant head. U.S. Pat. No. 7,955,355 to Chin describes extensions, although it does not teach the technique in which they are used to allow connecting rods to be placed. U.S. Pat. No. 7,918,858 to Stad et al. also describes extensions. The disclosure of U.S. Pat. No. 7,909,830 to Frigg et al. describes extensions and the surgical use of the extensions in conjunction with rod placement. These extended towers all have long slots in the sides. This is important to note, as rod placement by this approach is far too inaccurate to place directly within a spinal screw implant body. By extending the implant, it allows the surgeon to find the implant rod slot and introduce the rod higher and push it down until it seats in the implant body. There are self-evident issues with this approach. While less invasive than an open incision, there is muscle in the way, and the muscle must be split to allow the rod to slide downward into position within the spinal screw body. Secondly, the more screws the surgeon wishes to place, the more difficult the surgery becomes. Clearly such a procedure is limited in what it can do.

Therefore, while these prior minimally invasive spinal instruments and surgical procedures can be suitable for limited usage to which they somewhat address, they are not suitable to providing an instrument and surgical approach that can accurately and less traumatically place an implant connecting device over multiple levels.

Thus, a need exists to overcome the problems with the prior art systems, designs, and processes as discussed above.

SUMMARY OF THE INVENTION

The invention provides percutaneous minimally invasive access instrumentation and surgical procedures for percutaneous insertion of spinal implants that overcome the hereinafore-mentioned disadvantages of the heretofore-known devices and methods of this general type and that provide such features by substantially departing from the conventional concepts and designs of the prior art, and in so doing allow simpler and more accurate connection of multiple spinal implants while providing less trauma to soft tissue.

The present invention provides for a percutaneous access instrument for attachment to spinal implants, including posts that connect to the spinal implants.

The present invention provides for a percutaneous access instrument for attachment to spinal implants, including posts that connect to the spinal implants and a main body portion that can connect to at least one post.

The present invention provides for a percutaneous access instrument for attachment to spinal implants, including posts that connect to the spinal implants, a main body that can connect to at least one post, and a rod guide section attached to the main body.

The present invention provides for a percutaneous access instrument for attachment to spinal implants, including posts that connect to the spinal implants, a main body that can connect to at least one post, and a rod guide section attached to the main body, and a rod holder moveable within the rod guide.

The present invention provides for a percutaneous access instrument for attachment to spinal implants, including posts that connect to the spinal implants, a main body that can connect to at least one post, a rod guide section attached to the main body, a rod holder moveable within the rod guide, and the rod holder having a curvate shape.

The present invention provides for a percutaneous access instrument for attachment to spinal implants, including posts that connect to the spinal implants, a main body that can connect to at least one post, a rod guide section attached to the main body having bearings to allow smooth motion of the rod holder within the rod guide, the rod holder having a curvate shape that contacts the bearings.

The present invention provides for a percutaneous access instrument for attachment to spinal implants, including posts that connect to the spinal implants, a main body that can connect to at least one post, a rod guide section attached to the main body having bearings to allow smooth motion of the rod holder within the rod guide, and a portion of the rod guide that can be used to force the rod holder in contact with the bearings.

The present invention provides for a percutaneous access instrument for attachment to spinal implants, including posts that connect to the spinal implants, a main body that can connect to at least one post, a rod guide section attached to the main body having bearings to allow smooth motion of the rod holder within the rod guide, a second bearing section of the rod guide used to force the rod holder in contact with the bearings such that the curvate rod holder can rotate while in contact with the main body bearings and second bearing section.

The present invention provides for a percutaneous access instrument for attachment to spinal implants, including posts that connect to the spinal implants, a main body that can connect to at least one post, a rod guide section attached to the main body having bearings to allow smooth motion of the rod holder within the rod guide, and a second bearing section movable forward in an axial direction to exert force against the rod holder to hold it against the bearings or backwards to release pressure against the rod holder.

The present invention provides for a percutaneous access instrument for attachment to spinal implants, including posts that connect to the spinal implants, a main body that can connect to at least one post, a rod guide section attached to the main body having bearings to allow smooth motion of the rod holder within the rod guide, a rod secured to the rod holder, a second bearing section moved forward in an axial direction to exert force against the rod holder to hold it against the bearings, and the rod holder calibrated with markings that correspond to the length of the rod.

The present invention provides for a percutaneous access instrument for attachment to spinal implants, including posts that connect to the spinal implants, a main body that can connect to at least one post, a rod guide section attached to the main body having bearings to allow smooth motion of the rod holder within the rod guide, and a second bearing section movable forward in an axial direction to exert force against the rod holder to hold it against the bearings to allow the rod holder holding a rod to rotate to advance the tip of the rod through the skin and muscle.

The present invention provides for a percutaneous access instrument for attachment to spinal implants, including at least one post that connects to one or more spinal implants, a main body that can connect to at least one post, and a rod guide section attached to the main body which guides the tip of the rod secured in the rod holder accurately into at least one spinal implant.

The present invention provides for a percutaneous access instrument for attachment to spinal implants, including at least one post that connects to one or more spinal implants, a main body that can connect to at least one post, and a rod guide section attached to the main body which guides the tip of the rod secured in a calibrated rod holder accurately to a specific location within at least one spinal implant.

The present invention provides for a percutaneous access instrument for attachment to spinal implants, including at least one post that connects to one or more spinal implants, a main body that can connect to at least one post, and a rod guide section attached to the main body which guides the tip of the rod secured in a calibrated rod holder accurately to a specific location within at least one spinal implant, the calibrated rod holder having features for attaching a removable handle.

The present invention provides for a percutaneous access instrument for attachment to spinal implants, including at least one post that connects to one or more spinal implants, a main body that can connect to at least one post, and a rod guide section attached to the main body which guides the tip of the rod secured in a calibrated rod holder accurately to a specific location within at least one spinal implant, the calibrated rod holder having features for attaching a removable handle, and a section of the handle acting as a stop such that contact of the stop with a section of the main body stops further advancement of the rod and rod holder.

The present invention provides for a percutaneous access instrument for attachment to spinal implants, and a curvate rod holder which matches the curvature of the rod to be implanted.

The present invention provides for a percutaneous access instrument for attachment to spinal implants, and more than one curvate rod holder to allow rods of different curves or diameters to be used with the instrument.

The present invention provides for a percutaneous access instrument for attachment to spinal implants, more than one curvate rod holder to allow rods of different curves or diameters to be used with the instrument, and adjustable length posts to allow the instrument to compensate for different rod curvatures.

The present invention provides for a percutaneous access instrument for attachment to spinal implants, more than one curvate rod holder to allow rods of different curves or diameters to be used with the instrument, and multiple fixed length posts for each rod diameter to allow the instrument to compensate for different rod curvatures.

The present invention provides for a percutaneous access instrument for attachment to spinal implants, including at least one post that connects to one or more spinal implants, a main body that can connect to at least one post, and a rod guide section, and a open section of the main body having an opening to accept at least one additional post within the open section.

The present invention provides for a percutaneous access instrument for attachment to spinal implants, including at least one post that connects to one or more spinal implants and the main body, the posts having a keyway or feature to align the post relative to the rod slot in an implant.

The present invention provides for a percutaneous access instrument for attachment to spinal implants, including at least one post that connects to one or more spinal implants and the main body, the posts having a keyway or feature to align the post relative to the main body such that the main body is aligned parallel to at least one implant rod slot.

The present invention provides for a percutaneous access instrument for attachment to spinal implants, including at least one post that connects to one or more spinal implants aligned with the rod slot in an implant and the main body, and the main body with a secondary opening or slot that accepts a section of the post.

The present invention provides for a percutaneous access instrument for attachment to spinal implants and a main body, including a temporary attachment to a primary post that connects to one spinal implant, and a main body that can permit at least one additional post to fit within an opening or slot such that all posts are aligned to the main body and simultaneously aligned to the implants.

The present invention provides for a percutaneous access instrument for attachment to spinal implants, including at least one post that connects to one or more spinal implants, a main body that can connect to at least one post, and a rod guide section that can be advance to exert pressure against a rod holder or moved in an opposite direction to release pressure against the rod holder.

The present invention provides for a percutaneous access instrument for attachment to spinal implants and posts, a main body that can connect to at least one post, and a rod guide section that can be moved to release pressure against the rod holder and allow the main body to slide forward to reach a desired post.

The present invention provides for a percutaneous access instrument for attachment to spinal implants and posts, a main body that connects temporarily to one post, and a rod guide section that allows a rod holder holding a rod to be advanced in a curvate direction while permitting translational motion and adjustment by the sliding capability of the rod guide section.

The present invention provides for a percutaneous access instrument for attachment to spinal implants and posts, the posts having features to lock the posts to an implant.

The present invention provides for a percutaneous access instrument for attachment to spinal implants and posts, the posts having features to lock the posts to an implant while being cannulated to allow sliding over a k-wire and/or allowing access to the implant by screw drivers or other instruments.

The present invention provides for a percutaneous access instrument for attachment to spinal implants and posts, the posts having features to lock the posts to the inside of a spinal implant.

With the foregoing and other objects in view, there is provided, in accordance with the invention, a spinal implant device for inserting a curved spinal implant alignment rod through an opening of at least one spinal implant including a curved rod holder, an elongated main body, and at least one spinal implant post. The curved rod holder defines a central bore shaped to slidably receive therein the curved spinal implant alignment rod and having a rod holding curve substantially equal to a curve of the curved spinal implant alignment rod and has outer bearing surfaces. The elongated main body defines a post connector portion, a post receiving slot, and a rod holder slot and has a bearing assembly operable to hold the rod holder within the rod holder slot longitudinally and laterally stable and rotationally movable about a central rotation point of the rod holder that is aligned with the post connector portion. The bearing assembly has bearings providing at least three bearing contact points at the outer bearing surfaces to movably hold the rod holder with respect to the main body such that the rod holder can only arcuately rotate with respect to the central rotation point. The at least one spinal implant post has a distal implant retaining end operable to removably secure the at least one spinal implant thereto, a proximal post securing end shaped to removably secure with the post connector portion, and a height such that, when the proximal post securing end is removably secured at the post connector portion, the spinal implant is held at a distance to align the opening of the spinal implant with a tip of the rod in the rod holder when arcuate motion of the rod holder rotates the rod within the bearings to the spinal implant. The post receiving slot is shaped to hold the proximal post securing end longitudinally free and laterally secure. The rod holder slot is shaped to hold therewithin the bearings and to movably hold the rod holder within the bearings. At least one of the bearings is longitudinally adjustable towards and away from the rod holder to removably hold the rod holder therewithin.

In accordance with another feature of the invention, the rod is a set of rods having different curvatures, the rod holder is a set of rod holders correspondingly curved to the set of rods, the at least one spinal implant post is a plurality of posts each having a height such that, when the proximal post securing end is removably secured at the post connector portion, the spinal implant is held at a distance to align the opening of the spinal implant with a tip of the rod in the rod holder when arcuate motion of the rod holder rotates the rod rotated within the bearings to the spinal implant, and the bearings being adjustable to provide different holding geometries for the rod holders.

In accordance with a concomitant feature of the invention, there is provided a handle operable to rotate the rod holder within the main body. The handle has a handle end operable to stop rotation of the rod holder when a tip of the rod is in a defined location within the opening of the spinal implant.

Although the invention is illustrated and described herein as embodied in percutaneous minimally invasive access instrumentation and surgical procedures for percutaneous insertion of spinal implants, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Additional advantages and other features characteristic of the present invention will be set forth in the detailed description that follows and may be apparent from the detailed description or may be learned by practice of exemplary embodiments of the invention. Still other advantages of the invention may be realized by any of the instrumentalities, methods, or combinations particularly pointed out in the claims.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the present invention. Advantages of embodiments of the present invention will be apparent from the following detailed description of the exemplary embodiments thereof, which description should be considered in conjunction with the accompanying drawings in which:

FIG. 7 is a fragmentary, perspective view of a side the rod holder of FIG. 5;

FIG. 8 is a fragmentary, perspective view of a front of the rod holder of FIG. 5;

FIG. 9 is a fragmentary, enlarged, perspective view of a front end of the rod holder of FIG. 5;

DETAILED DESCRIPTION OF THE INVENTION

Figure 1:
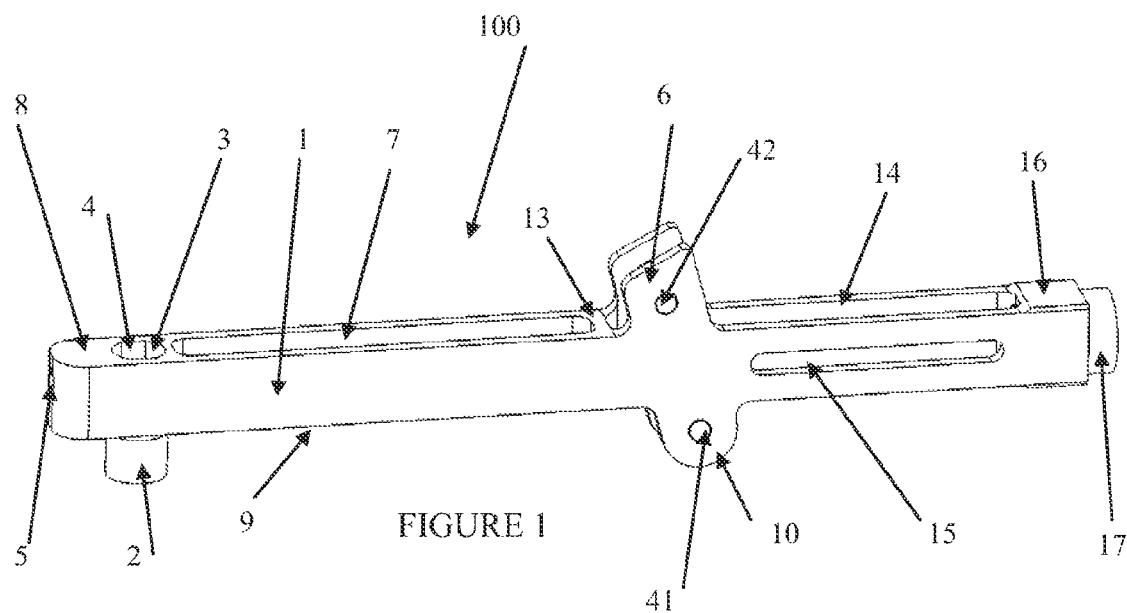
FIG. 1 is a perspective view of a main instrument body from a side thereof.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises ... a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

Herein various embodiments of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Figure 10:
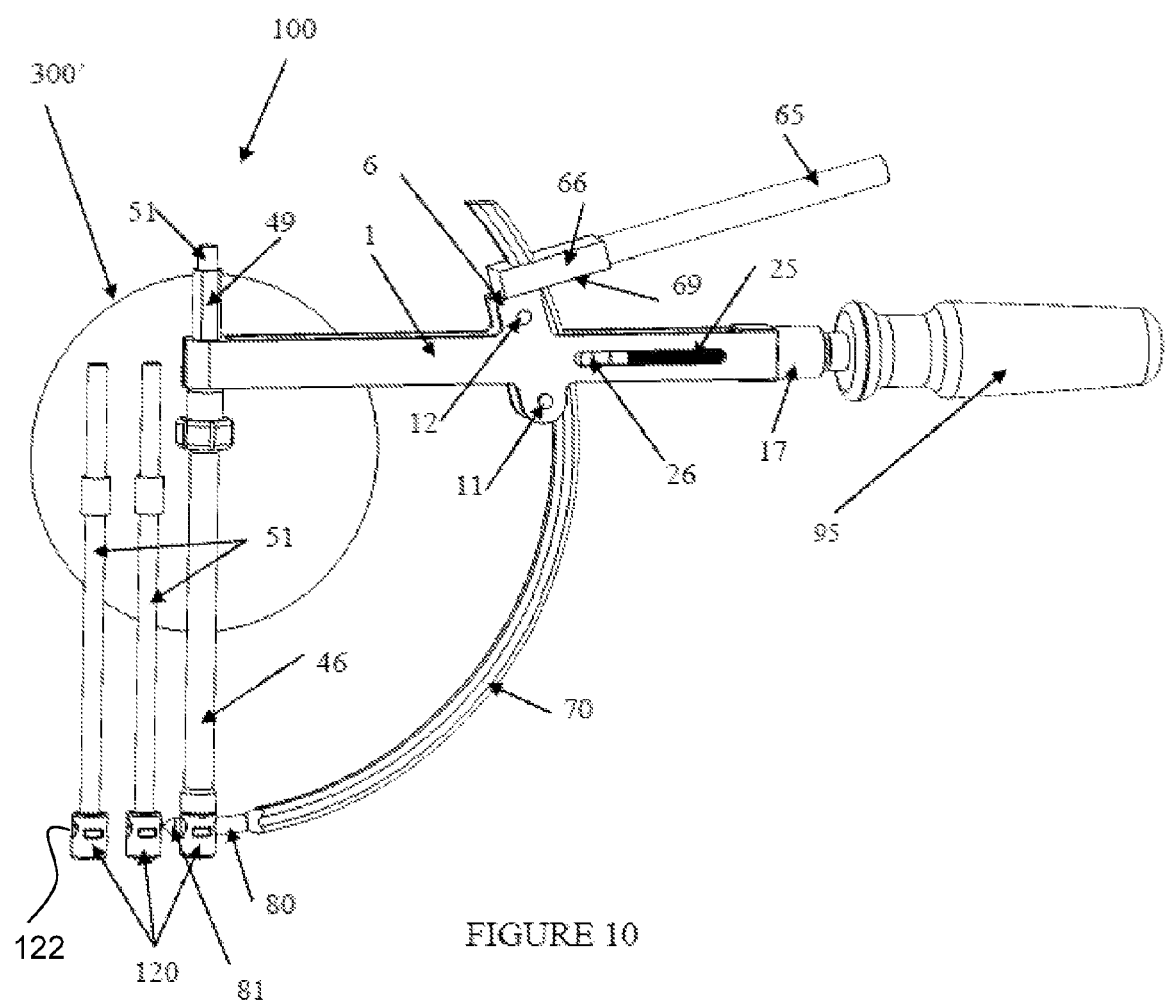
FIG. 10 is a perspective view of a side of the instrument assembly of FIG. 2 attached to a first post and a spinal screw assembly with the rod disposed inside one spinal implant.

Described now are exemplary embodiments of the present invention. Referring now to the figures of the drawings in detail, there is shown a first exemplary embodiment of a new instrument, illustrated generally at 100 in FIGS. 1 through 14, that, by its novel construction, permits the instrument 100 to lock onto guide posts attached to implants (an example of which is shown in FIG. 10 as element 120) and allows the introduction of a rod member through one or more implants by rotation and translation capability.

The main body 1 is substantially rectangular in shape. Of course, the main body 1 does not need to be rectangular, but can also be other shapes. The main body 1, as well as the other components of the instrument can be made of various materials, such as, but not limited to, metals, such as aluminum, titanium, or stainless steels, polymers, or a combination of both.

The main body 1 has various features shown in FIG. 1. These features include an extension 2 having an opening 3 and an alignment keyway 4, the opening extending into or through a portion of the main body 1 and the keyway formed in at least one section of the extension 2. The main body 1 is also slotted 7, with the slot 7 extending through from the top 8 of the main body 1 to the bottom 9 of main body 1. A threaded hole or other feature 5 is optionally machined into the main body 1 at the tip. A rear slot 14 is also provided in the main body 1, with a bridge portion 13 provided between the two sections to add rigidity to the main body 1. The bridge portion 13 is optional and may not be necessary when the main body 1 is constructed from rigid materials. The rear slot 14 is intersected by a slot 15 through the side of the main body 1. Between the front slot 7 and rear slot 14 is disposed a bearing section having an upper portion 6 and a lower portion 10, with the upper portion 6 having a through-hole 42 and the lower portion 10 having a through-hole 41. At the end of the instrument 100 is a threaded nut 17, which is attached to the end 16 of the instrument 100 or is simply machined into the material at the end 16 of the instrument 100.

Figure 2:
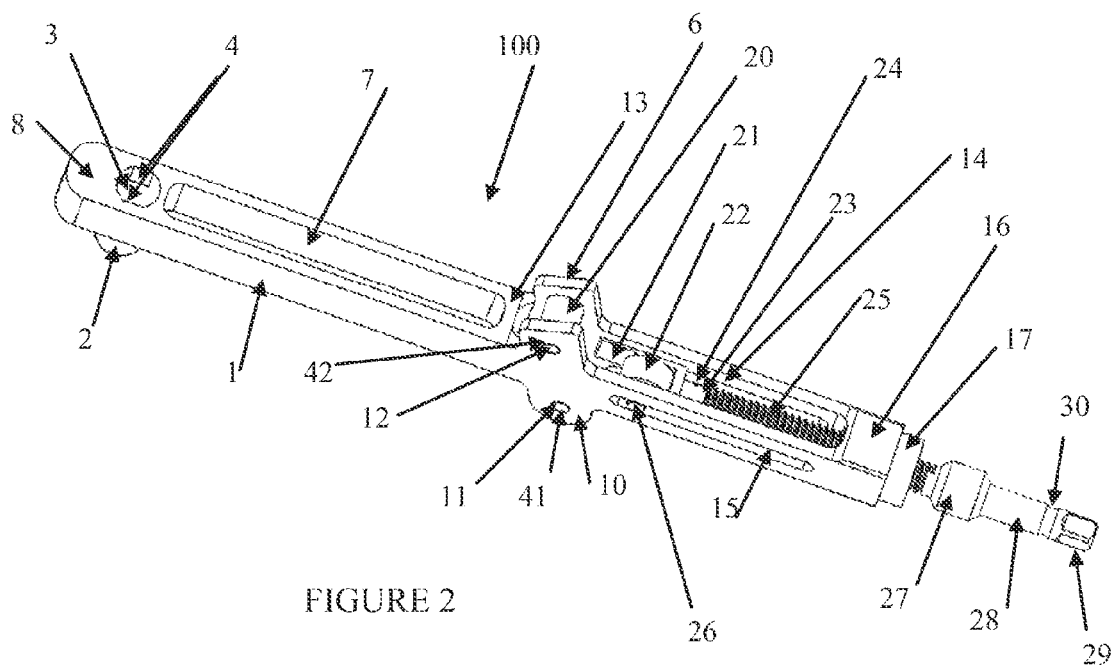
FIG. 2 is a perspective view of the main instrument body of FIG. 1 with a rod assembly.
Figure 3:
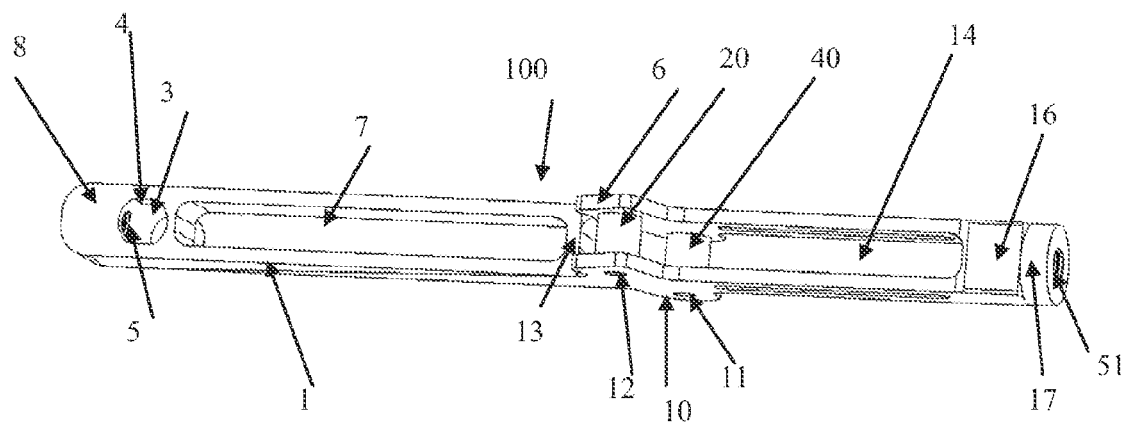
FIG. 3 is a perspective view of the main instrument body of FIG. 1.

In FIGS. 2 and 3, the main body 1 is further expanded by the addition of other components. Within hole 41, a pin 11 is inserted through a bearing 40, and a pin 12 is inserted through hole 42 and bearing 20. The bearings 20 and 40 are free to rotate around their respective pins 12 and 11. The pins 11 and 12 can be press fit, threaded, welded, or otherwise secured in place in holes 41 and 42 without effecting the rotation of the bearings 20 and 40. Furthermore, an additional bearing 22 is held within a carrier 21 and secured by a pin 26. This bearing 22 is free to rotate about pin 26. In addition, the pin 26 also is long enough to stay within the slot 15 in the main body 1. The width of slot 15 is slightly larger than the diameter of the pin 26. This permits the bearing 22, carrier 21, and pin assembly to slide axially with the pin 26 in slot 15. A threaded rod 25 (or threaded rod section) is attached to the carrier 21 to allow the end of the thread to freely rotate while still being attached to carrier 21. This is further detailed in FIG. 5, whereby the carrier 21 has an extension 60 with a groove 61. The extension 60 fits into a hole in a portion of the threaded rod 25 such that the groove 61 is suspended within the hole. The groove aligns with a hole in the threaded rod end 23 and is pinned to hold the carrier 21 in contact with the threaded end 23 while allowing the threaded end 23 to turn freely. Of course, there are other ways to attach the carrier 21 and threaded rod end 23. Also shown in FIG. 2 is that the threaded rod 25 has an end 27. The threaded rod can be machined with the end 27 as one piece, or attached by pinning, soldering, welding, press fitting, or a combination of techniques. This allows the threaded rod 25 to be purchased as a finished component and subsequently attached to the end 27. The end 27 can, then, be connected directly to a handle 95 that is fixed, as shown in FIG. 10, or provided with an attachment device operable to connect to a handle 95 that is removable. In FIG. 2, this is shown as a square drive attachment having a square end 29, a groove 30, and an extension 28 to allow a square drive handle to engage and temporarily lock the handle to the end 27 fixed to the threaded rod 25.

As the threaded nut 17 is either integral with the end 16 of the main body 1 or is rigidly attached, it cannot move relative to the main body 1. Thus, when the threaded rod 25 is turned, the carrier 21, bearing 22, and pin 26 move axially either towards the front of the instrument or back, depending on the direction the threaded rod 25 is turned. Furthermore, the speed in which the carrier 21 is advanced can be controlled by the type of thread (i.e., pitch) on the threaded rod 25. By using a multiple start ACME thread instead of a single start, each turn of the handle can advance the carrier 21 at up to 4 times faster than the standard ACME thread. Such a configuration is advantageous in that it avoids constant turning of the handle to move the carrier 21 back and forth inside the main body 1. For this to function, the threaded nut 17 has an internal thread that matches the thread used on the threaded rod 25.

Figure 4:
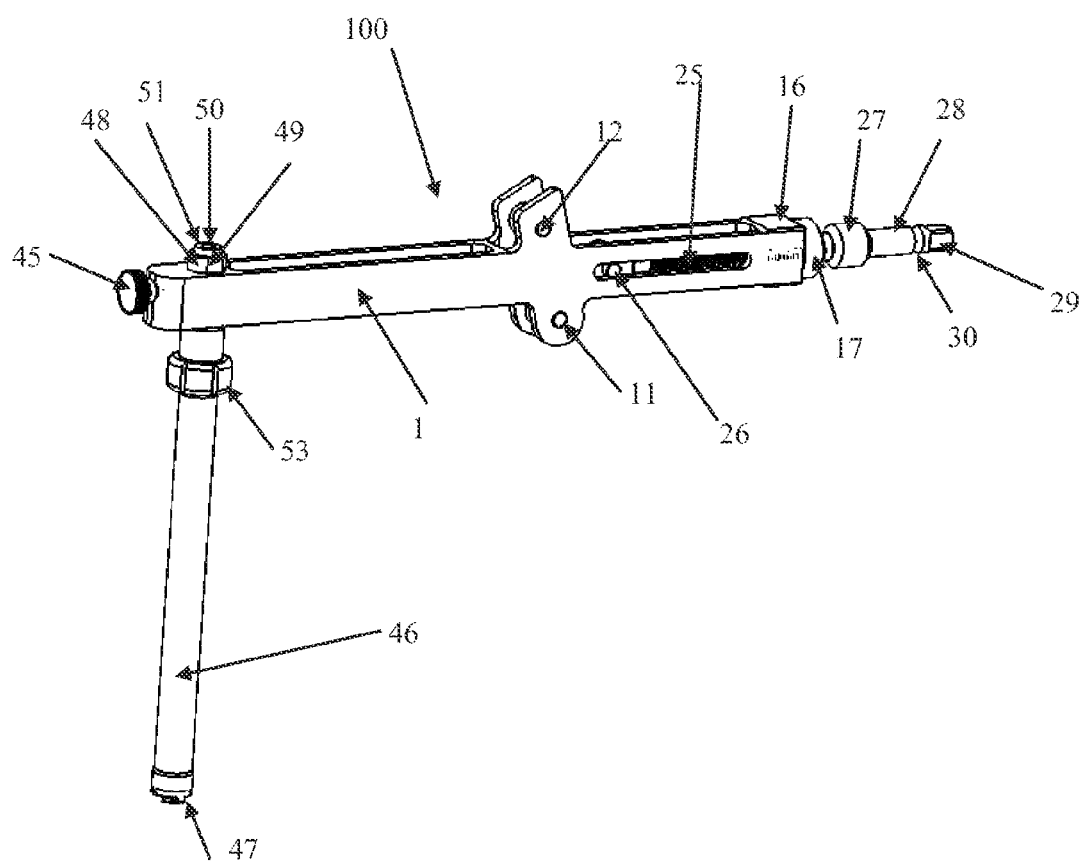
FIG. 4 is a perspective view of the main instrument of FIG. 2 with a single post.

In FIG. 4, the assembly generally indicated as 100 is shown attached to a post 46. The post 46 has features for interfacing the instrument 100 and includes a section 48 that slides within the opening 3 in the main body 1 and the extension 2 and a keyway 49 for engaging the keyway 4 in the main body 1. An internal shaft 51 is cannulated, having a hole 50 that runs through the entire length of shaft 51. The shaft 51 is configured to be held within the post 46 and locked to the spinal implant. It can also be locked to the main body 1 by a spring loaded plunger 45. The use of a lock is optional, and friction is usually sufficient to hold the post 46 in place. The implant end of the post 46 has alignment tabs 47 that align the post 46 to the spinal implant. This allows the spinal implant to be aligned to the post 46 and the post 46 to be aligned to the main body 1.

Figure 5:
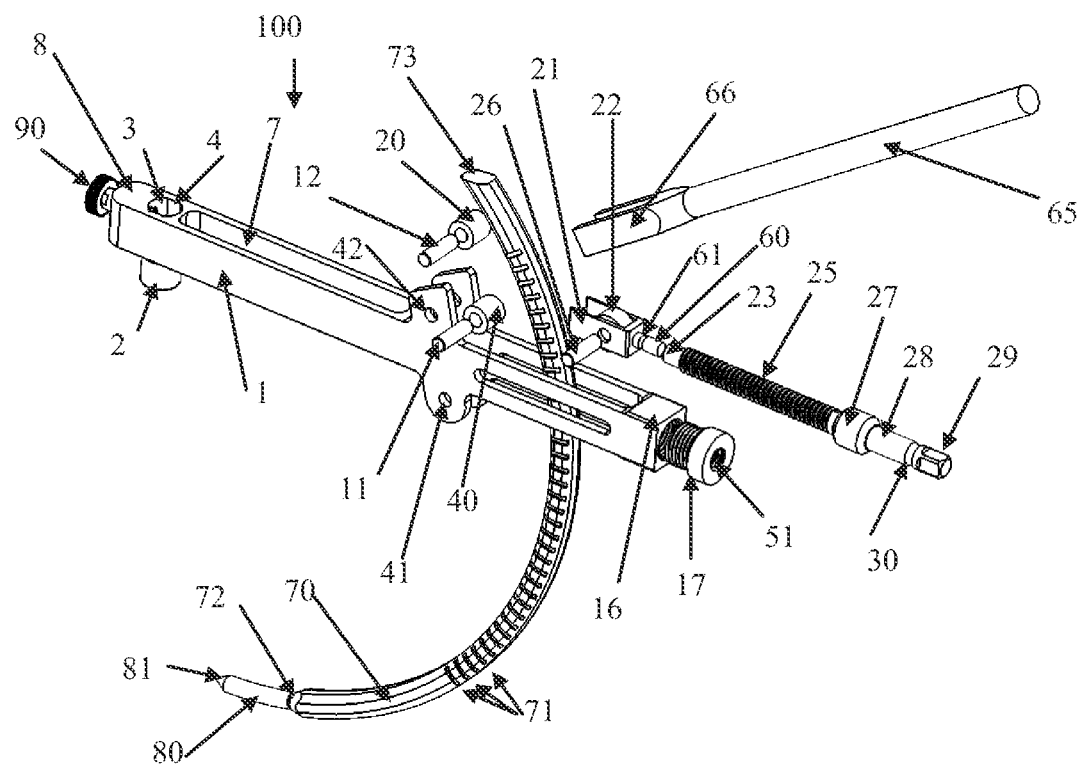
FIG. 5 is an exploded, perspective view of the instrument assembly with a rod holder, a rod, and a rod advancement handle.

In FIG. 5, the instrument assembly is shown with the rod holder 70. The rod holder 70 is configured to secure and hold a rod 80 at the rod securing end 72 of the rod holder 70. This rod securing end 72 is tapered to minimize resistance and trauma to soft tissue as it enters. The rod 80 is curved to match the curve of the rod holder 70. The tip 81 of the rod 80 is generally pointed to allow the rod 80 to drive through soft tissue and help guide itself into, for example, a slot 122 within the spinal implant 120 (see FIG. 10). The assembly of the rod 80 and rod holder 70 can also be considered a curved needle. Between the end 73 of the rod holder 70 and the rod securing end 72 are attachment features 71 for attachment of a handle 65. The attachment features 71 are shown here as grooves, but they can also be holes, extensions, or other features that allow engagement with handle 65. The handle 65 has an end 66 that connects to the features 71 to provide a somewhat rigid connection. This connection allows force to be applied to the rod holder 70 such that the rod holder 70 can be advanced or retracted through the soft tissue and spinal implants. The attachment features 71 are calibrated relative to the length of the rod 80. Thus, the handle 65, when attached to the features 71, acts as a stop when it contacts the upper face of portion 6 of the main body 1.

Figure 6:
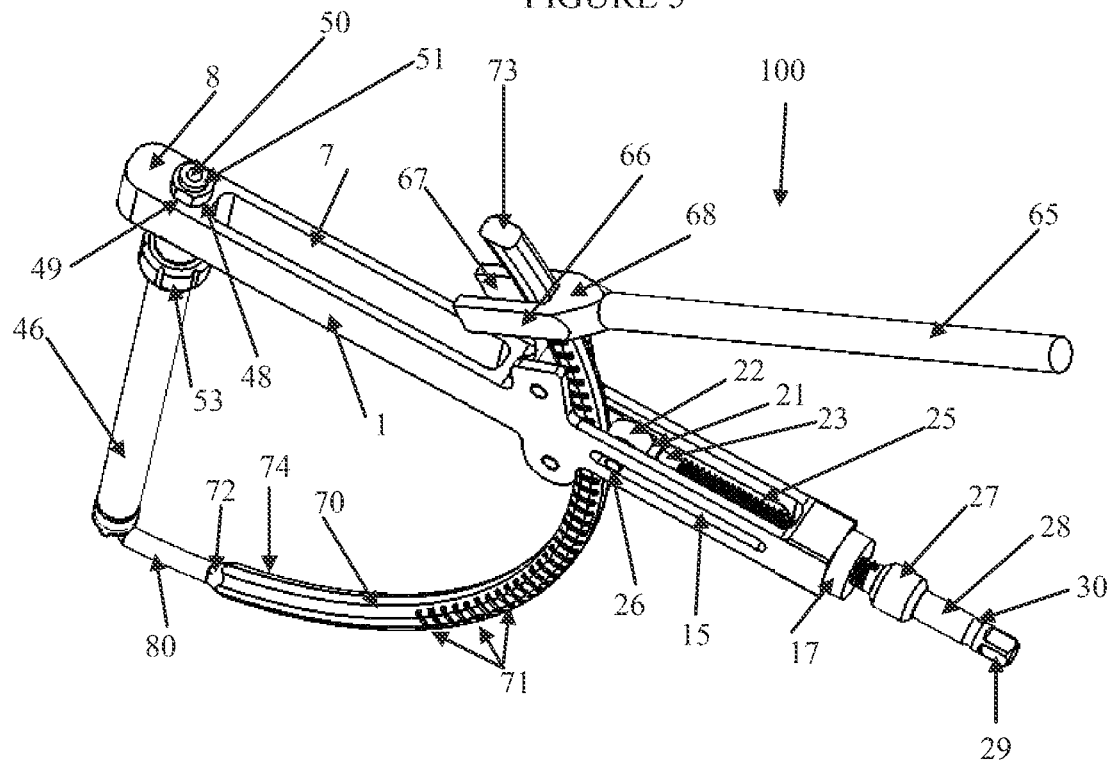
FIG. 6 is a perspective view of the instrument assembly of FIG. 5 with the rod advancement handle engaged with the rod holder and with an implant post.

FIG. 6 shows the instrument generally identified with 100 along with the rod holder 70 securely held between bearings 22 and bearings 20 and 40 (shown in FIG. 5). By using three bearings 20, 22, 40, the curved rod holder 70 rotates in an arc based on the bearing geometry. The geometry is configured to place the tip 81 of the rod 80 approximately perpendicular to the post 46 and main body hole 3 when the rod 80 is guided to the proper position. The height of the post 46 is also important in determining exactly where the tip 81 of the rod 80 will be after rotation.

In FIGS. 7, 8, and 9, the rod holder 70 is further detailed. The rod holder 70, generally identified with reference 200, includes grooves 71, a rod securing end 72 or tapered tip as discussed previously, an end 73, and flat surfaces 74 and 74'.

The flat surfaces 74, 74' provide bearing surfaces to mate the rod holder 70 with the bearings 20, 22, 40. A hole 75 in the end of rod holder 70 is machined with a keyway 77 so that the rod 80 with a matching end can be secured in the rod holder 70 while permitting the curve of the rod 80 to be aligned with the curve of the rod holder 70 and to be held in such alignment during insertion of the rod 80 into the spinal implants.

FIG. 10 shows the first step in use of the instrument assembly 100. The instrument assembly 100 is depicted with the rod holder 70 held against the three bearings such that the rod holder 70 can only rotate. The height of post 46 is configured such that that the opening in the implant to accept the rod 80 (e.g., slot 122 of spinal implant 120) is the correct location based on the arcuate motion of the rod holder 80 when rotated within the bearings. It is noted that the arcuate motion is configured so that the center of rotation of the arc is vertically aligned with the hole 3 in the main body 1. The horizontal alignment can be varied according to the rod holder 70 curvature, bearing geometry, and height of the post 46. This novel approach allows for rods of different curvature to be used by altering the posts, the rod holders, and/or the bearing geometry. It is further noted that the end 66 of the handle 65 stops the rod holder 70 when the rod tip 81 is in the exact desired location. This is significant because, in minimally invasive surgery, visualization of the location of the rod tip is not easy and is, often, impossible. Thus, the stop is a way for the surgeon to determine that the tip is within the spinal implant.

Once the rod 80 is within the first spinal implant 120, the threaded rod 25 is turned by the handle 95 to release pressure off the rod holder 70 and to back the carrier 21 out of the way. Continuing from FIG. 10, where the first spinal implant 120 has the rod 80 within it, the released pressure off the rod holder 70 allows the instrument 100 to slide forward.

Figure 11:
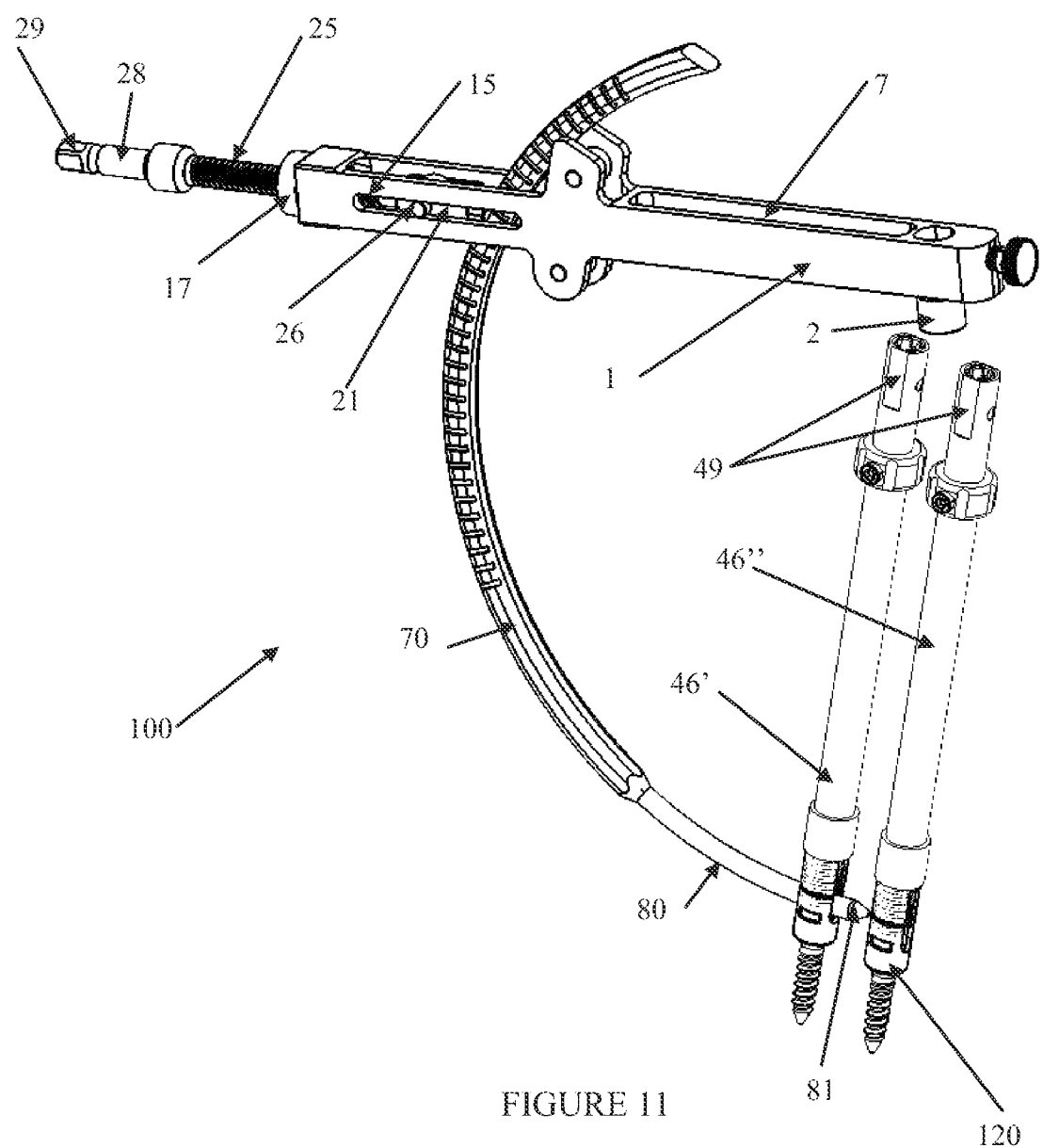
FIG. 11 is a perspective view of a side of the instrument of FIG. 10 aligned with first and second posts to place the rod within one implant and with the instrument free of both posts.

FIG. 11 depicts the instrument 100 removed off the first post, re-defined as 46', and slid partially forward towards the second post 46".

Figure 12:
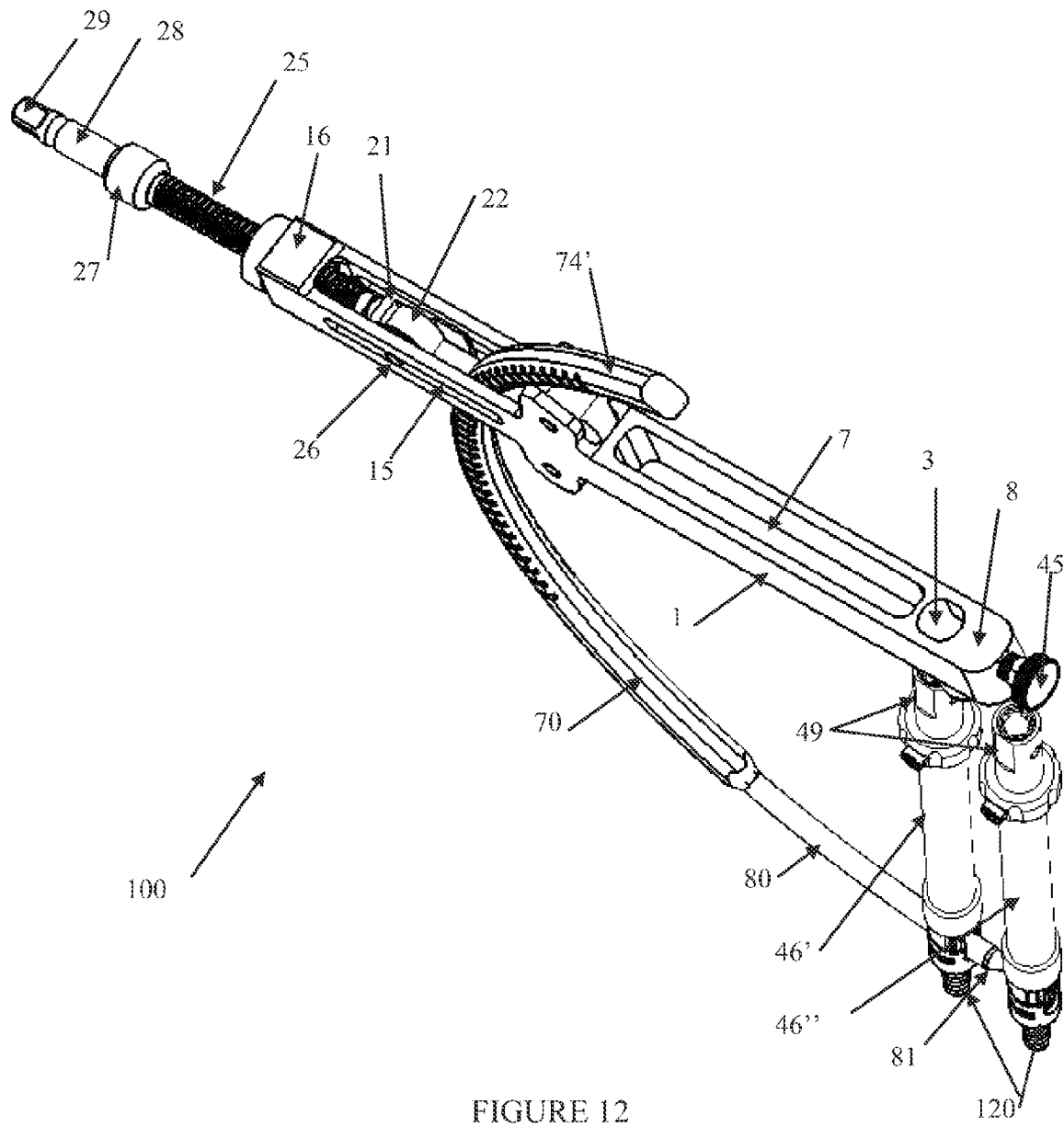
FIG. 12 is a perspective view from above the instrument of FIG. 11.

FIG. 12 clarifies the procedure as, from the top view, it can be seen that the bearing 22 in the carrier 21 is well out of the way and not in contact with the rod holder 70. This gap allows the instrument 100 to slide forward so that hole 3 can be placed at the next post 46".

Figure 13:
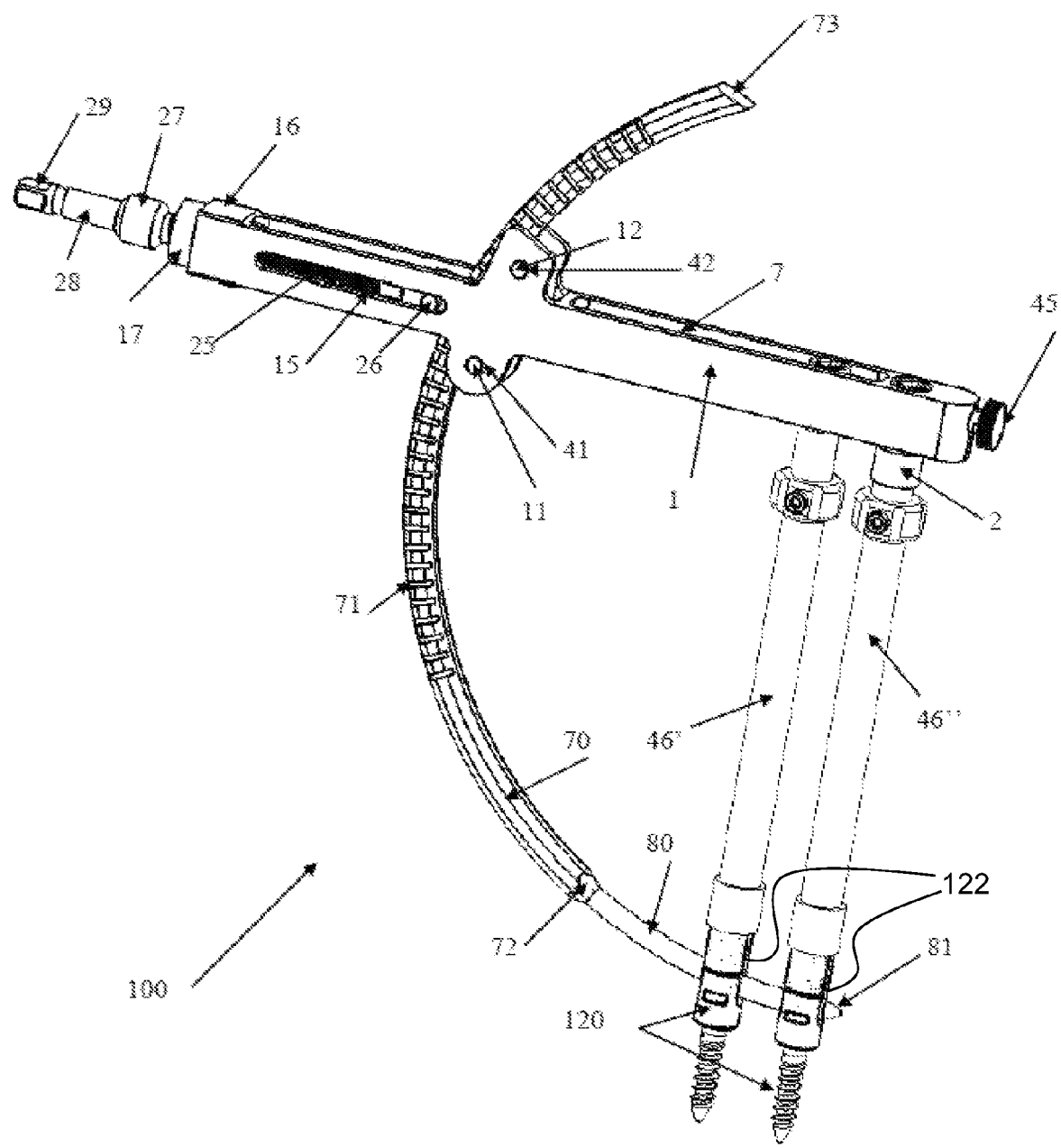
FIG. 13 is a perspective view of a side of the instrument of FIG. 10 attached to the second post with the first post contained within the instrument body to align the posts and allow the rod to enter multiple spinal implants.
Figure 14:
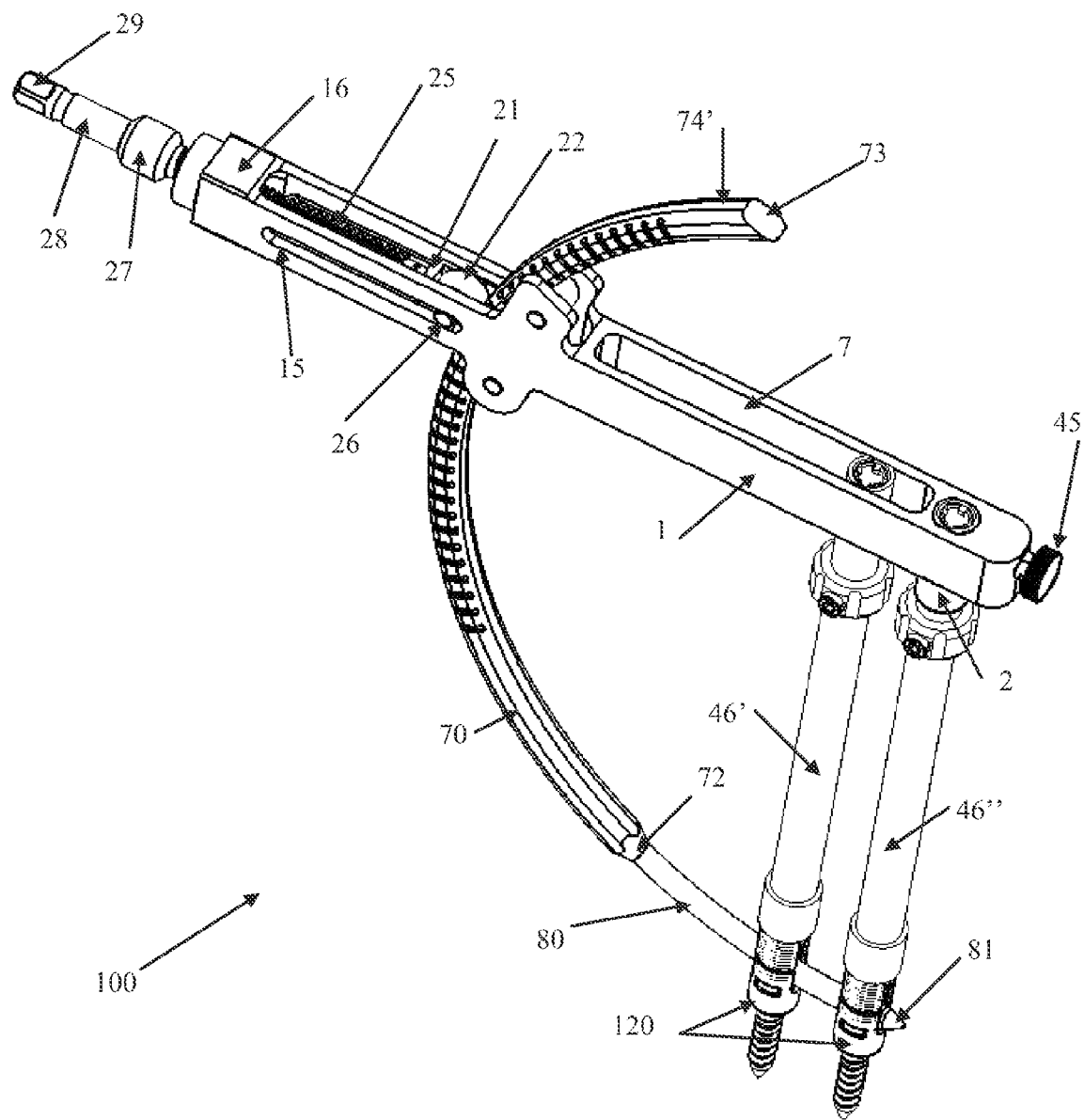
FIG. 14 is a perspective view from above the side of the instrument of FIG. 13.

In FIGS. 13 and 14, the hole 3 of the instrument 100 is aligned with the post 46" and the post 46' is aligned with the slot 7 in the main body 1. When the instrument 100 is seated on post 46", post 46' slides into slot 7. As the posts 46', 46" are keyed relative to the spinal implants 120, the post in the slot (here 46') also aligns the spinal implant 120 to the instrument 100. This aids in aligning the rod slot 122 in the spinal implants 120. Although not always necessary, the instrument 100 provides a novel way of aligning the rod slots 122 when hidden by the restrictions of minimally invasive access. Even though only two posts 46', 46" are depicted in the slot 7, more than two of the posts can slide within the slot 7.

With the posts 46' and 46" in position, the threaded rod 25 is turned to press the bearings 20, 40, and 22 against the rod holder 70. Then, the rod holder 70 is rotated using the handle 95, which forces the tip 81 of the rod 80 through the next spinal implant 120.

From this, it can be understood that advancing the rod 80 through multiple spinal implants 120 is a stepwise progression of rotation and axial motion. Every time the instrument 100 is advanced to the next post, the rotation point moves with it. Such movement effectively allows the instrument 100 to be moved up or down the spine while advancing the rod 80 through as many spinal implants 120 as necessary or desired.

Figure 15:
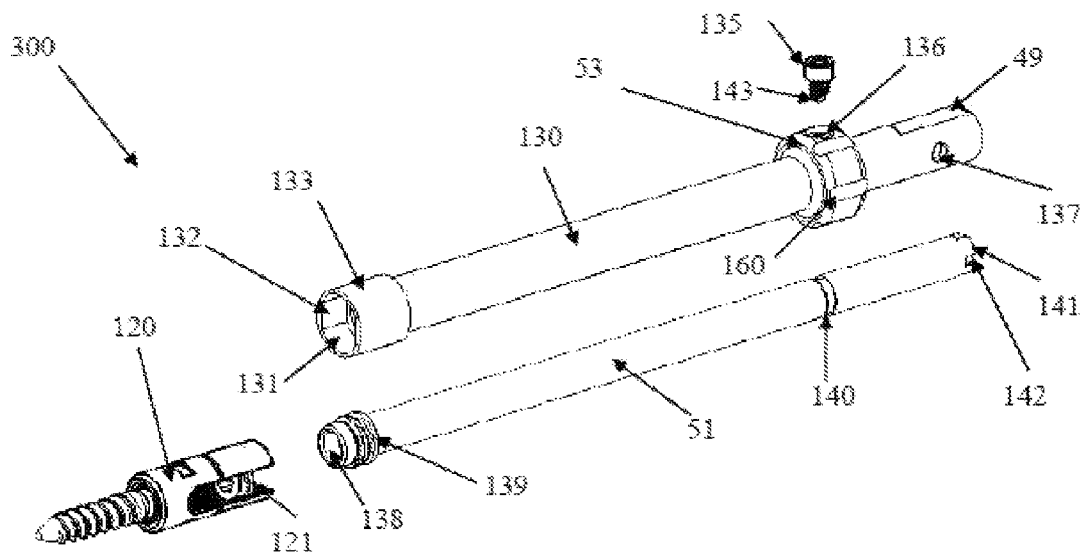
FIG. 15 is an exploded perspective view of another exemplary embodiment of a post assembly.

FIG. 15 depicts an exemplary embodiment of a post 300. In this exploded view, the post 300 includes an outer body 130 with a hole 131 and keyway 132 for fitting over and aligning with a spinal implant 120. The outer body 130 also has a hole though its entirety for accepting an internal shaft 51. The outer body 130 also has a knob 53 to provide the surgeon measures for turning the spinal implant 120 by hand to aid in aligning the rod 80 to the instrument 100, a keyway or flat 49 for aligning the outer body 130 to the instrument 100, and a screw 135 having a tip 143 shaped to fit into a groove 140 in the internal shaft 51. A lateral hole 137 allows a portion of the plunger 45 to slide therein to lock the outer body 130 to the main body 1 when needed. The internal shaft 51 has a cannulated end 138 to allow screwdrivers and k-wires through the middle, while having a feature 139 to engage and hold the spinal implant 120. As shown, reference numeral 139 represents threads, however, this feature can be a myriad of other connection options, including bayonet, tabs, or other locking measures to hold onto the spinal implant 120. The internal shaft 51 is free to rotate within the outer body 130 and is held positionally to the outer body 130 by engagement of the tip 143 of screw 135 in the groove 140 of the internal shaft 51.

Figure 16:
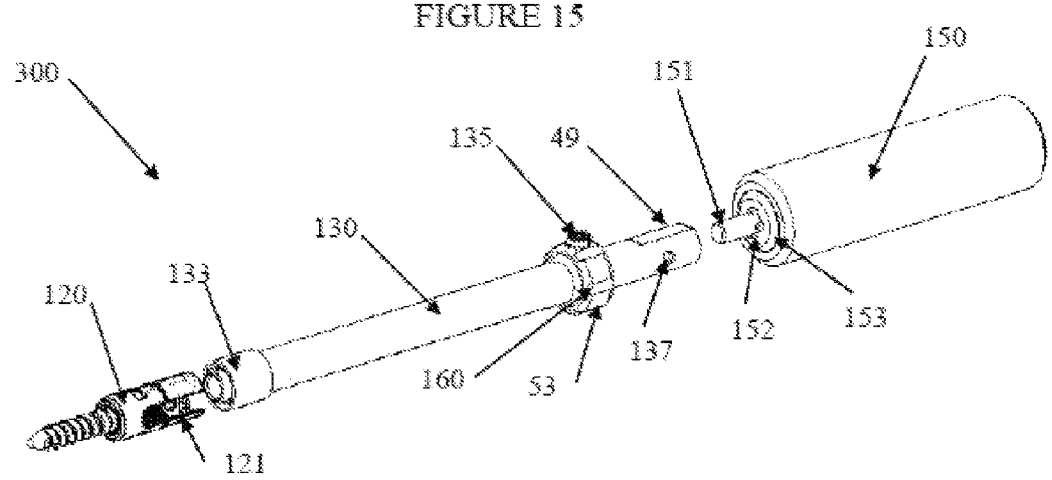
FIG. 16 is an exploded perspective view of the post of FIG. 15 assembled and with the assembly handle.
Figure 17:
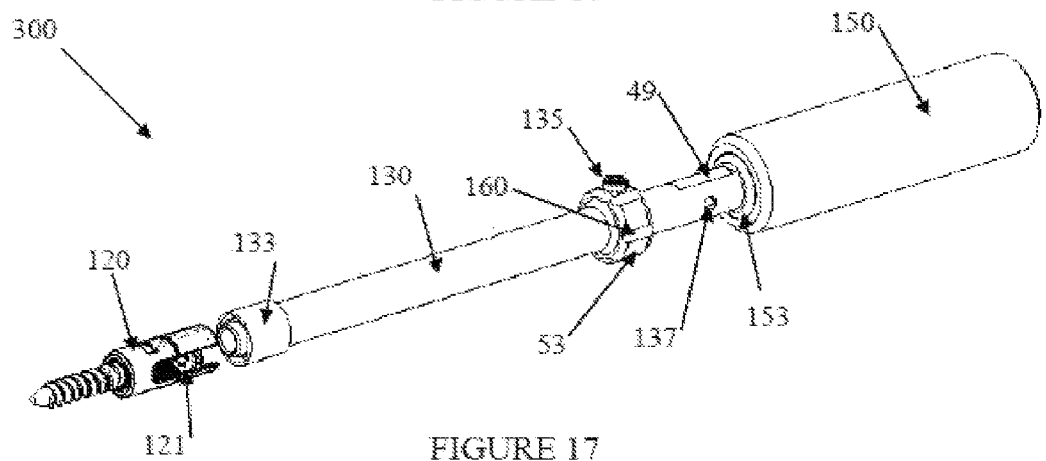
FIG. 17 is an exploded perspective view of the post of FIG. 16 with the assembly handle engaged with the post.

Features for allowing the internal shaft 51 to be moved in such a way as to force the internal shaft 51 to engage and hold the spinal implant 120 are provided. As shown as one possibility, end 141 has grooves or notches 142 for engagement of an instrument handle 150 to permit turning of the internal shaft 51, which handle 150 is shown in FIGS. 16 and 17. The handle 150 has a raised feature 153 to aid in keep the surgeon's gloves away from being pinched and projections 152 that are configured to interface with the grooves or notches 142 in the internal shaft 51.

Figure 18:
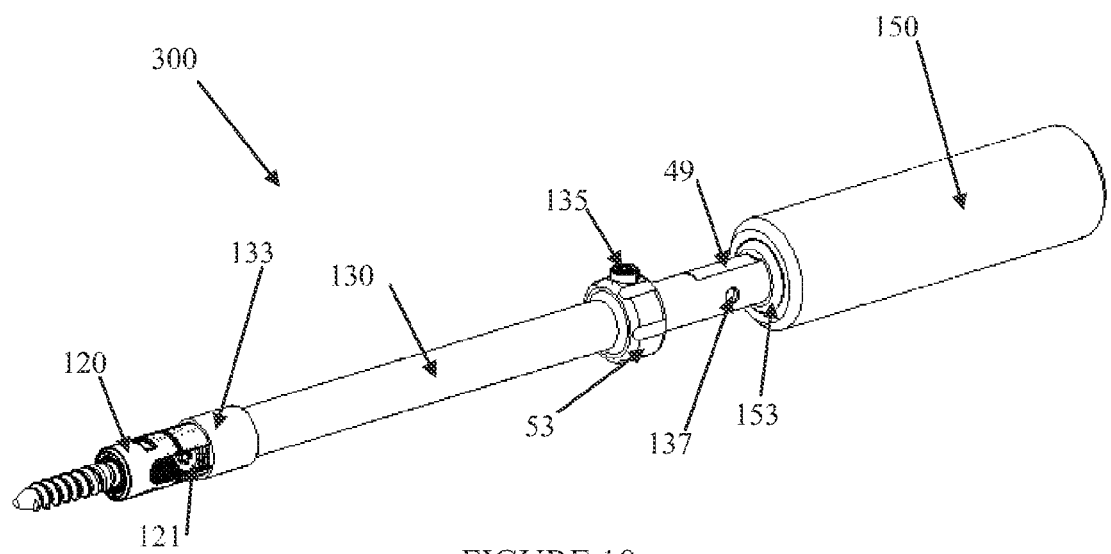
FIG. 18 is a perspective view of the post of FIG. 17 showing that, by turning the assembly handle, the post engages and locks to a spinal implant.

In FIGS. 16, 17, and 18, the handle 150 is turned to engage the threads 138 on the internal shaft 51 with internal threads on the spinal implant 120. Once the corresponding threads are tightened, the handle 150 is removed, leaving the post assembly 300 secured to the implant 120. The post 300, as it is cannulated, can remain attached until the spinal implant 120 is secured to the rod 80.

Also shown in FIGS. 16, 17, and 18, is that the measures used to lock the spinal screw to the rod can be placed and held within the body of the spinal implant 120 during the procedure. In this example, a set screw 121 is held in the spinal screw during rod insertion. This eliminates the step of adding a locking component after rod insertion. This is only possible due to the unique and novel approach set within. By using a controlled arc with axial motion, the tip 81 of the rod 80 can be very accurately placed, thus allowing room for a set screw or other locking measures.

Figure 19:
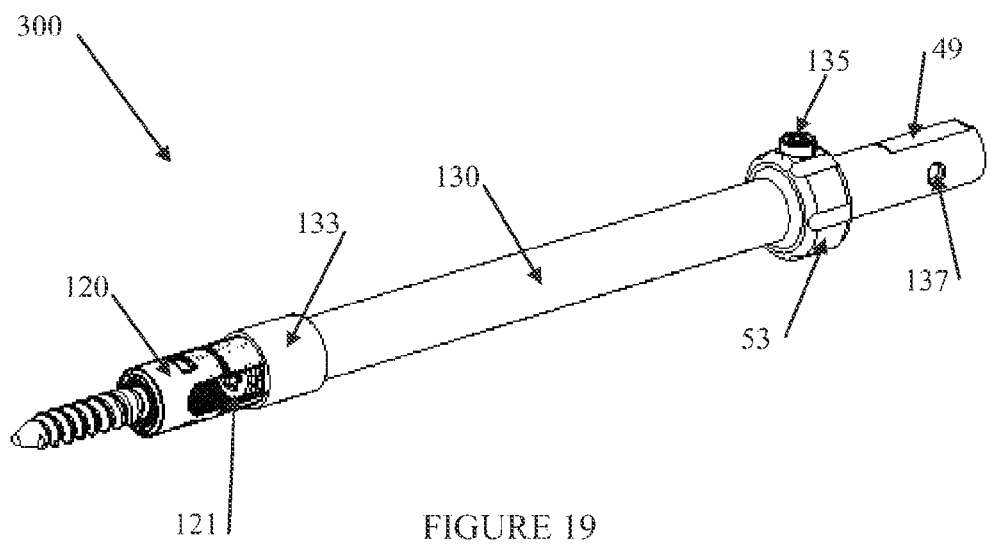
FIG. 19 is a perspective view of the post of FIG. 17 locked to the spinal implant ready for use and without the assembly handle.
Figure 20:
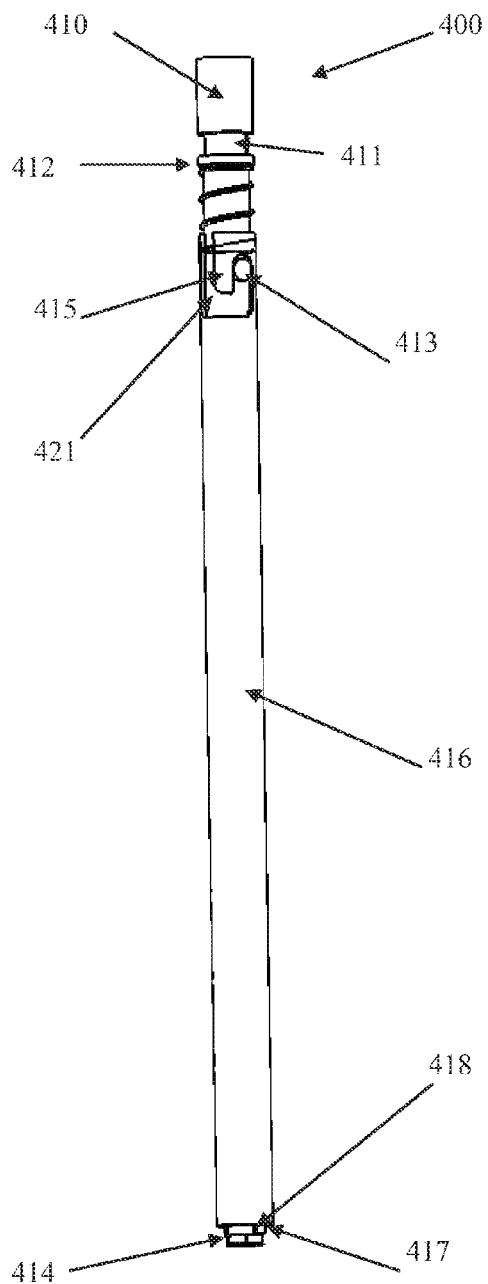
FIG. 20 is a side elevational view of an alternative exemplary embodiment of a post attachment mechanism for attachment to a spinal implant.
Figure 21:
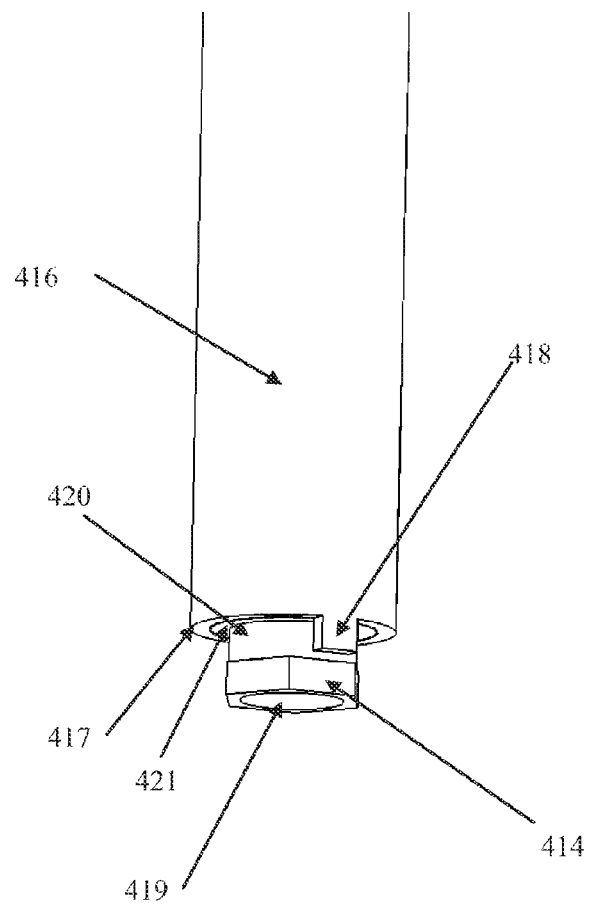
FIG. 21 is an enlarged perspective view of an implant attachment end of the post attachment mechanism of FIG. 20.
Figure 22:
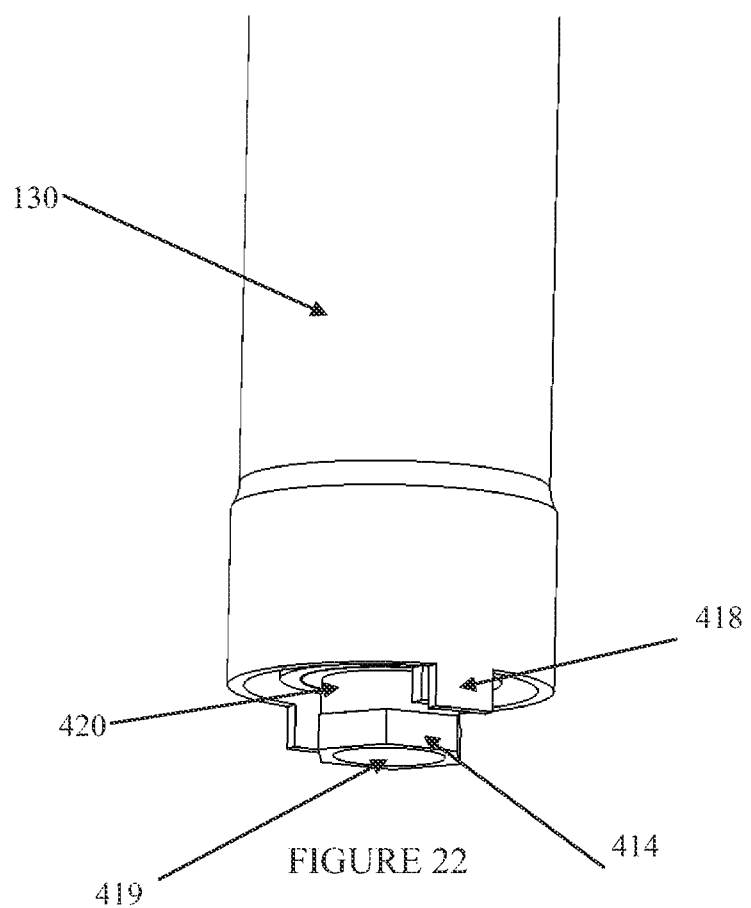
FIG. 22 is an enlarged perspective view of the implant attachment end and post assembly of FIG. 20.

An alternative post structure, as generally represented as 400, is shown in FIGS. 20, 21, and 22. For this example, an inner shaft 421 has a hex 414 machined into it. A recess 420 is cut above the hex into the inner shaft 421. The hex 414 fits within a hex machined into a spinal implant rod securing device, such as the set screw 121 in FIG. 19. The hex in the set screw 121 is the same height as the recess 420. Thus, when the hex 414 is inserted into the hex in set screw 121, the recess 420 is aligned with the hex in the set screw 121, and hex 414 drops below the lower surface of the hex in set screw 121. This allows the inner shaft 421 to turn, as the recess 420 moves freely within the hex. When the hex 414 on the inner shaft 421 is turned, the hex in the set screw 121 and the hex 414 on the inner shaft 421 becomes misaligned. By rotating the hex 414 an angle of 30 degrees, the points of hex 414 are exactly in the middle of the flats of the hex in the set screw 121. This misalignment acts as a temporary lock to hold the set screw 121 to the inner shaft 421. Of course, the misalignment angle must be held, otherwise the shaft 421 and set screw 121 will disengage. Therefore, an outer sleeve 416 is provided, having engagement features 418, e.g., teeth or tabs. This outer sleeve 416 is connected by a bayonet feature 415, which allows the outer sleeve 416 to remain physically attached to the inner shaft 421 while allowing the outer sleeve 416 to move up and down. A pin 413 machined on the inner shaft 421 provides the engagement feature for the bayonet 415. A spring 412 exerts force against the outer sleeve 416 to push it downward toward the hex 414. By using a set screw having grooves or slots that match the engagement features 418 formed in the outer sleeve 416, the assembly generally shown as 400 can be inserted into the hex of the set screw 121, and turned to a set angle, thereby allowing the engagement features 418 to slide into the grooves or slots in set screw 121. This allows the hex of the set screw 121 to align in a locking position with the hex 414 of the inner shaft 421 and be securely held at the correct locking position. To release assembly 400, pulling up on the outer sleeve 416 disengages the engagement features 418 from the slots or grooves in the set screw 121, allowing the assembly 400 to be turned until the hex in the set screw 121 and inner shaft 421 align, allowing the assembly 400 to be pulled off. Also shown is groove 411, which is aligned to allow the plunger 45 to hold the assembly 400 securely in the instrument generally shown as 100. The assembly 400 is, then, inserted into a outer body 130 of the post shown in FIG. 22. This post 130 is similar in shape to post 46; however, post 130 also has features 418 to engage the spinal implant 120. This allows the post 130 to engage and align with the implant 120 such that flats on the top of the post 130, as shown in previous figures can be aligned relative to the rod slot 122 in the spinal implant body 120.

The present invention, as mentioned previously, allows the curved rod holder 70 to be of any radius and matched to the desired radius of the rod 80. This is a unique advantage over prior art, as the curvature of the spine varies from patient to patient, and one size does not fit all. In addition, the curved rod holder 70 and instrument structure as generally shown in 100, primarily relies on the curved rod holder 70 and curved rod 80 to place the tip 81 of the rod 80 within the spinal implant 120. Once the tip 81 of the rod 80 is within the spinal implant body 120, the rod 80 is linearly advanced by advancing the instrument assembly 100 to the next post 46. As this approach is a combination of linear and curved motion, the instrument does not need all spinal implants to be on the same curve for purposes of introducing the rod 80. In addition, the length of the rod 80 can be of almost any practical length according to what is needed for the particular patient and number of spinal implants needed.

To allow rod holders 70 and rods 80 of different curvatures to work, the relative curve radius increases or decreases the distance of the tip of the rod 80 to the projected center of a spinal implant connected to a post. This change can be compensated for by adjusting the height of the post. Depending on the curvature of the rod holder 70, it may also be necessary to adjust the location of the bearings 20 and 40. This adjustment can be done by providing a single instrument with a main body 1 that allows the bearings to be moved, or by providing more than one instrument assembly, generally shown as 100, in an instrument set. Offsetting the location of the hole 3 in the main body 1 can also be done to change the location of where the bearings are located relative to where the post 46 contacts the spinal implant 120. This can be done through a main body 1 having a modular nose or section to allow different lengths to be snapped in place, or again by multiple single non-modular instruments in a set.

The foregoing description and accompanying drawings illustrate the principles, exemplary embodiments, and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A spinal implant device for inserting a curved spinal implant alignment rod through an opening of at least one spinal implant, comprising:
    a curved rod holder:
        defining a central bore shaped to slidably receive therein the curved spinal implant alignment rod and having a rod holding curve substantially equal to a curve of the curved spinal implant alignment rod; and
        having outer bearing surfaces;
    an elongated main body defining a post connector portion, a post receiving slot, and a rod holder slot and having a bearing assembly operable to hold the rod holder within the rod holder slot longitudinally and laterally stable and rotationally movable about a central rotation point of the rod holder that is aligned with the post connector portion, the bearing assembly having bearings providing at least three bearing contact points at the outer bearing surfaces to movably hold the rod holder with respect to the main body such that the rod holder can only arcuately rotate with respect to the central rotation point;
    at least one spinal implant post having:
        a distal implant retaining end operable to removably secure the at least one spinal implant thereto;
        a proximal post securing end shaped to removably secure with the post connector portion; and
        a height such that, when the proximal post securing end is removably secured at the post connector portion, the spinal implant is held at a distance to align the opening of the spinal implant with a tip of the rod in the rod holder when arcuate motion of the rod holder rotates the rod within the bearings to the spinal implant;
    the post receiving slot being shaped to hold the proximal post securing end longitudinally free and laterally secure; and
    the rod holder slot being shaped to hold therewithin the bearings and to movably hold the rod holder within the bearings, at least one of the bearings being longitudinally adjustable towards and away from the rod holder to removably hold the rod holder therewithin.

2. The spinal implant device according to claim 1, wherein:
    the rod is a set of rods having different curvatures;
    the rod holder is a set of rod holders correspondingly curved to the set of rods;
    the at least one spinal implant post is a plurality of posts each having a height such that, when the proximal post securing end is removably secured at the post connector portion, the spinal implant is held at a distance to align the opening of the spinal implant with the tip of the rod in the rod holder when arcuate motion of the rod holder rotates the rod rotated within the bearings to the spinal implant; and
    the bearings being adjustable to provide different holding geometries for the rod holders.

3. The spinal implant device according to claim 1, which further comprises a handle operable to rotate the rod holder within the main body, the handle having a handle end operable to stop rotation of the rod holder when the tip of the rod is in a defined location within the opening of the spinal implant.

\* \* \* \* \*